United States Patent [19]

Hermann, Jr. et al.

[11] Patent Number: 4,852,560
[45] Date of Patent: Aug. 1, 1989

[54] TOXICOLOGY SPECIMEN COLLECTION SYSTEM

[75] Inventors: William J. Hermann, Jr., Sealy; John R. Zanek, Missouri City, both of Tex.

[73] Assignee: 501 North American Biotechnology, Inc., Sealy, Tex.

[21] Appl. No.: 186,267

[22] Filed: Apr. 26, 1988

[51] Int. Cl.⁴ .............................................. A61B 5/00
[52] U.S. Cl. ...................................... 128/762; 4/144.1
[58] Field of Search .............. 128/760, 762; 604/317; 4/144.1, 144.2

[56] References Cited

U.S. PATENT DOCUMENTS

| | | | |
|---|---|---|---|
| D. 221,911 | 9/1971 | Ericson | D24/54 |
| D. 231,273 | 4/1974 | Olsson | D24/54 |
| 3,561,427 | 2/1971 | Profy | 128/762 |
| 3,894,845 | 7/1975 | McDonald | 128/762 |
| 3,943,770 | 3/1976 | McDonald | 73/421 R |
| 4,026,433 | 5/1977 | Crippa | 128/760 |
| 4,042,337 | 8/1977 | Griffith | 128/762 |
| 4,559,649 | 12/1985 | Burnett | 4/144.1 |
| 4,736,859 | 4/1988 | Mayes et al. | 4/144.1 |

OTHER PUBLICATIONS

P-Splitter ®, Helena Plastics brochure.
QualEx TM, LabelCo, Inc. brochure.

*Primary Examiner*—Max Hindenburg
*Attorney, Agent, or Firm*—Fitzpatrick, Cella, Harper & Scinto

[57] ABSTRACT

A secure specimen collection vessel is provided, which in a preferred embodiment comprises a four-chamber base cup, 1, a twist-lock antirotation cap, 2, and a resilient sealing plug, 3. Clip-off drain tabs, 6, and vent tabs, 7, are located at the bottom end of the base cup, allowing each chamber to be drained individually for repeat analysis of a urine sample. The locking, antirotation cap, 2, prevents the contents of the vessel from being accidentally contaminated by the external environment, and also assures that any attempt to forceably remove the cap, 2, will result in visibly obvious damage to the collection vessel.

6 Claims, 3 Drawing Sheets

TOXICOLOGY SPECIMEN COLLECTION SYSTEM

BACKGROUND OF THE INVENTION

1. Field of the Invention:

The present invention generally relates to urine specimen collection vessels, and specifically to a secure specimen collector which is designed to address the liability and security considerations of employee drug testing.

2. Brief Description of the Prior Art:

Known urine collection containers are illustrated by the following U.S. Pat. Nos. ERICSON Des.221,911; OLSSON Des.231,273; MCDONALD 3,894,845; MCDONALD 3,943,770; CRIPPA 4,026,433; GRIFFITH 4,042,337; BURNETT 4,559.649.

The above patents generally relate to collection containers for obtaining urine specimens for medical analysis. The patent to GRIFFITH, for example, discloses a time collection device for urine, constructed so as to create an integrated specimen by means of a receptacle divided into bin sections. A removable manifold cover is adapted to fit on top of a receptacle portion, and the manifold has openings arranged to be in registration with each bin section, so that substantially equal amounts of urine enter each section, for separate rest purposes.

A P-Splitter ® urine proportioning device recently was introduced by Helena Plastics of San Rafael, Calif. The device comprises a two-outlet funnel and a pair of taped-together specimen containers. The lid design of each container is of the locking type, but requires a special tool and is intended to be repeatedly opened for separate testings. Further, the funnel fits into separate entry holes in each specimen container, and these holes are merely plugged, with stoppers.

A QualEx TM urine collection and mailing system recently was introduced by LabelCo, Inc. of Minneapolis, Minn. The device comprises a single chamber cup, with a top that has a first, inner seal, a double seal under a cap, and a third pressure-sensitive security seal, around the cap. Any such single chamber device is considered too vulnerable to post-collection tampering. A second area of vulnerability involves use of pressure sensitive seals or tapes for the security sealing process. Adhesive seals or tapes can be removed and replaced without leaving clear evidence of unwanted entry into the sample container.

The present invention, by contrast, defines four chambers so that each one of a multiple series of tests actually is made upon a different chamber of a single container, without destroying the integrity of any other chamber. Once any single chamber container has been opened for presumptive testing, a reasonable doubt exists as to whether any foreign substance entered during the time interval between the presumptive, or first, test and any later, or confirmatory, tests.

The private and governmental sectors currently are placing an increasing emphasis on drug testing of employees, particularly for those individuals whose job performance affects the personal safety of other people, e.g., pilots, bus drivers, police officers, etc. Because of the severe consequences of a positive result, it is common practice to verify all positive results with one or more confirmatory tests. In order to assure that every analysis is made on the same specimen, it is extremely beneficial to have the original sample separated into multiple parts at the time of collection.

Modern drug testing procedures, therefore, require not only an integrated specimen for repeat analysis, but also a specimen of high integrity which the tester knows has not been accidentally contaminated or intentionally tampered with in any manner. It is essential that the employer be certain that the specimen being tested is that of the person for whom the request was made. There is a real threat of a legal challenge to a legitimate positive result due to a minor error of record keeping detail during collection or handling. If specimen integrity is to be maintained during testing of each aliquot of the urine specimen, there cannot be any intermixing of contents among the individual chambers, and there must also be a way to prevent aspiration of specimen from a chamber into the atmosphere, or into contact with the body of a technician.

None of the prior art urine collection vessels provide or suggest means for guaranteeing specimen integrity from the time of collection to the end of the analytical operations.

OBJECTS AND SUMMARY OF THE INVENTION

Accordingly, it is a first object of the present invention to provide a specimen collector vessel that will prevent intentional tampering with the contents of the vessel.

A second object of the present invention is to provide a specimen collector vessel that will prevent the specimen from being accidentally contaminated by the external environment.

A third object of the present invention is to provide a specimen collector vessel that forces a sample to be distributed in equal aliquots into a plurality of chambers, while also providing means to empty each chamber individually, without the possibility of intermixing the contents of any of the chambers. An option is a handle that fits around the multi-chambered container, that can be removed after the collection has been made.

A complete toxicology collection system essentially comprises a tamper-resistant collection vessel, characterized by a four-chambered base container, a one-time self-locking lid with an associated seal, and a central resilient plug adapted to seal off the equal distribution entry ports into the individual chambers of the base container. The total system further comprises chain-of-custody documentation forms, which can be supplemented with a legal opinion letter to ensure adherence to proper collection procedures. A step-by-step procedure is included with the kit to eliminate many of the commonplace mistakes currently made. It is essential to the examining authority that every specimen tested was handled in an exacting manner. The chain of custody document asks for documentation of every person, including witnesses, who had access to the specimen. A well documented handling history is required if litigation concerning the collection and handling procedure arises.

The total system preferably is individually stored and shipped in a sturdy corrugated shipping box with a molded, or vacuum formed, fitted insert designed to hold container, lid, and banding seals. The collection system preferably is received by the collection agent in a sealed package, with all items of the kit under a single clear wrapper. This wrapper can be peeled back to gain access to the kit accessories. The system further may comprise a set of four cutting tools, (one to remove the vent and drain nipples associated with each chamber); an inking disc (used to affix a thumbprint to the lid); a lid labelling disc to be afixed to lid; and a lid sealing disc protector or moisture barrier.

The collection vessel is multi-chambered. During the collection procedure, a specimen automatically is separated into, preferably, four independent chambers. The vessel is designed in such a way that the chambers can be accessed on an individual basis without affecting the integrity of the specimen in the adjoining chambers. Hence, multiple dispensing, for repeat analyses, is possible without the problem of contamination or compromise of total specimen integrity, after the cap is sealed upon the base container. Once the lid is secured after collection, it cannot easily be reopened. Access to the sealed specimen is impossible without an obvious destruction to the container, that will alert a clinician performing a later test that an unauthorized entry was attempted.

Once a specimen is poured into the central receiving portion of the container, the cap is applied over the open top of the container and is ready to make a first and a second engagement with the container. Thereafter, only approximately 1/16th of a turn is required to permanently lock the cap onto the container. A resilient annular seal, between the cap and the container upper edges, closes off the open top of each chamber. Once the cap is locked in place, removal can only be made by breaking the series of locking tabs on the inside of the cap and the outside of the container, thereby leaving an indication that the specimen has been compromised. It is important to note that the cap never has to be removed in order to test a specimen, since sets of drain and vent nipples are located at the bottom of the container. The nipples are injection-molded as part of the polypropylene base cup, must be cut to be removed and thereafter cannot be resealed. The four chambers completely are sealed one from the other by a central core plug, of a resilient rubber material. The plug material acts as a slide valve and also is subjected to an axial compression, to enhance closure of each equal distribution entry port. The rubber used is tested for known leaching and absorption characteristics, as is the resin used to injection mold the base cup.

If four cutting tools are supplied, a new cutting tool can be used for removing the set of drain and vent nipples providing access into a chamber to be tested. Each chamber preferably is individually lettered or numbered. It is recommended that the chambers be tested starting with the chamber marked "A" or "1", and the further testing follow sequentially thereafter (B, C, and D, or 2, 3, and 4).

Various printed matter is preferably directly associated with each collection vessel. A circular label is supplied that is to be affixed to the outside top of the lid. This label is designed to contain the signature (or initials) of the collector and the employee; a thumb print of the employee; the date of collection; the kit/specimen control number; and the employee I.D. number. A small ink pad also may be provided to facilitate affixing the employee thumb print onto the circular label. Complete collection, handling, transportation, and storage instructions preferably are printed on a surface of the container, or on an inside surface of the shipping package. The chain-of-custody documentation can be physically connected to the collection vessel by a cord, to serve as a reminder that each person handling the specimen, from the time of collection to the final disposition of the specimen, is to acknowledge his custody. It is also preferred that five pressure sensitive labels, each containing the same control number, be part of the kit. The same control number label can be affixed to the container, to the chain of custody documents, to the outer box, to a spare for lab roster, and to a certification document.

Having now provided a brief summary of the invention, a preferred embodiment will now be described with reference being made to the accompanying drawings.

DESCRIPTION OF THE PREFERRED EMBODIMENT

Figure 1:
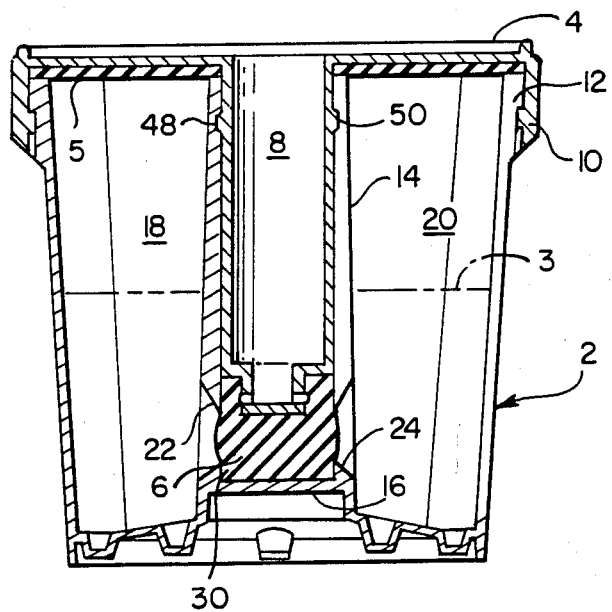
FIG. 1 is a side elevation, assembly view, in partial section, of a sealed specimen collection assembly according to a preferred embodiment of the present invention.

The preferred urine specimen collector assembly depicted in a vertical section elevation view in FIG. 1 generally comprises a four-chamber base cup, 2, a twist-lock antirotation cap 4, that supports a resilient sealing plug, 6, at the distal end of an axial sealing plug support, 8. The base cup, 2, and cap, 4, are constructed of an F.D.A. grade polypropylene, that is substantially inert to urine. The cap may be colored or opaque, but the cup preferably is substantially clear.

Details of the base cup, 2, further are shown in FIGS. 3, 7, 8, and 9. There are four receiving chambers (A, B, C, D) with each approximately 70 c.c. in volume. Hence, a total specimen volume of about 280 cc. can be colected. Four equal distribution ports (22, 24, 42, 44) provide communication between a central fluid passageway, 30, and each of the four receiving chambers. Each chamber has a separate set of drain nipples (34A, 34B, 34C, 34D) and vent nipples (36A, 36B, 36C, 36D) that are located at the bottom end of the cup, to permit each fluid receiving chamber to be emptied individually. The nipples are injection molded as part of the cup base, and are protected from damage by a surrounding rim, or base flange, 46.

Figure 3:
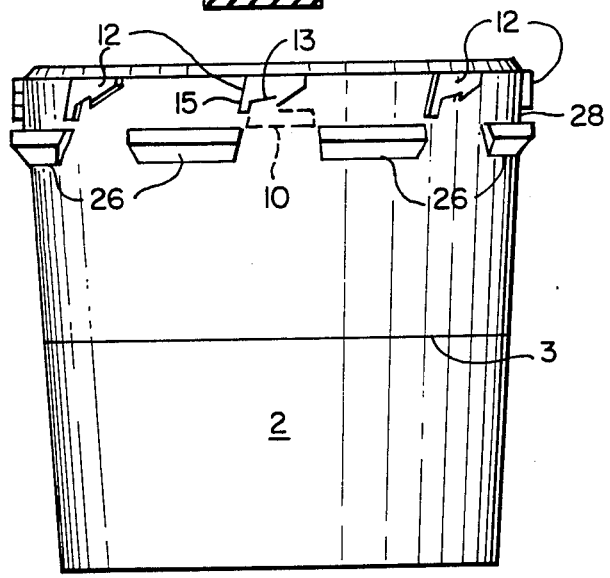
FIG. 3 is a side elevation view of a preferred base cup container portion of the specimen collection vessel.
Figure 4:
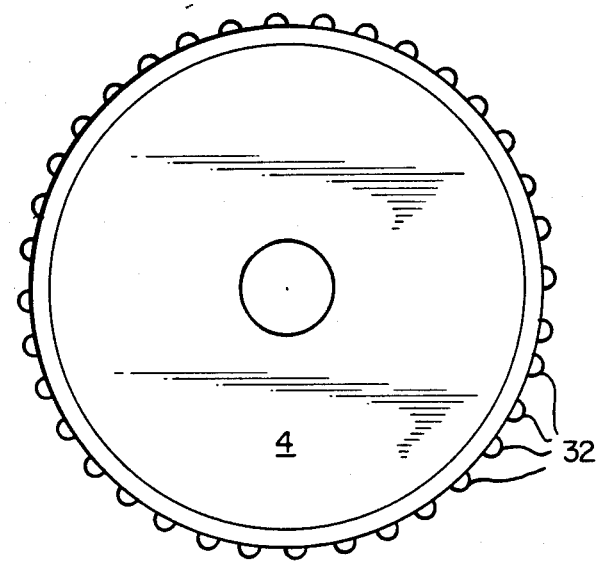
FIG. 4 is a top plan view of the cap shown in FIG. 2.

As best shown in FIG. 3, proximate the upper end of the base cup are disposed a plurality of cup lock tabs, 12, with each having a ramp, 13, and a downwardly extending stop extension, 15. The cup ramp surfaces, 13, are configured to engage, in a ratchet-like manner, with oppositely disposed ramp surfaces, 17, of each cap lock tab, 10. Each cap lock tab, 10, ramps into a separate lock with a cup tab, 12, and each cap tab is prevented from over-rotation by the frangible stop extension 15. A series of cup ratchet guides, 26, not only sets the cap lock tabs into a proper initial position prior to locking, but also acts to prevent reverse rotation of the cap by creating spaces that each cap lock tab will axially move into.

FIG. 1 shows an annular resilient seal cap liner, 5, made of an F.D.A. approved material, located between the bottom of cap, 4, for closing off the top of each compartment. An axial locking action urges the cap liner tightly against the upper edges of the chambers. To ensure a good seal, a first engagement by the cap and cup locking tabs is supplemented by a second engagement by a thread means that is disposed between the outer surface of the central support for the reesilient sealing plug, and the inner wall of the central receiving passageway.

Figure 2:
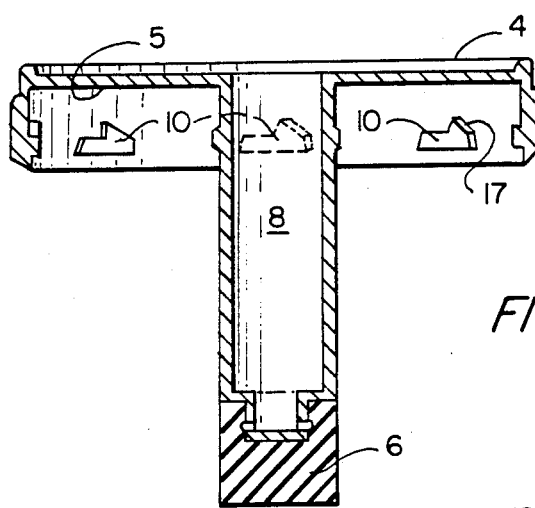
FIG. 2 is a side elevation view, in partial section, of a preferred cap portion of the specimen collection vessel.
Figure 5:
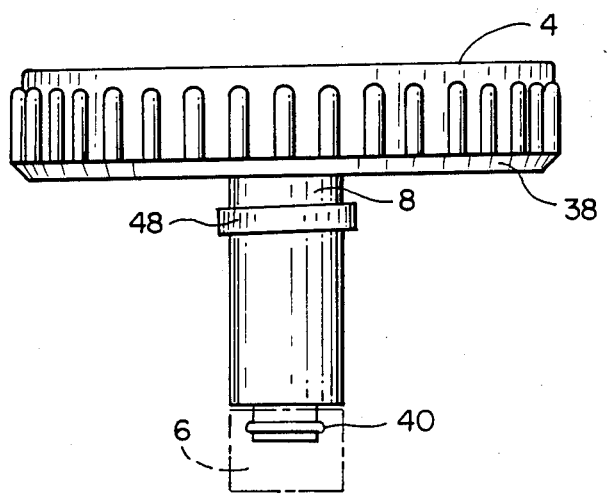
FIG. 5 is a side elevation view of the cap shown in FIG. 4.
Figure 6:
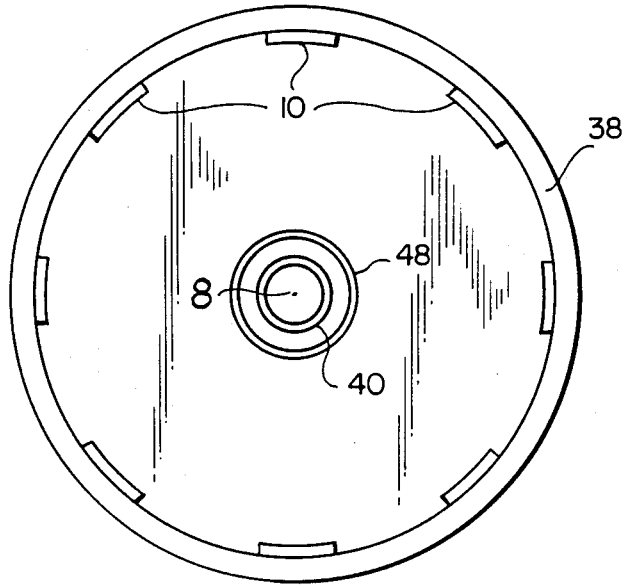
FIG. 6 is a bottom plan view of the cap shown in FIG. 4.

Further preferred construction details of the antirotation cap, 4, are illustrated in FIGS. 2, 4, 5, and 6. The cap has knurls, 32, on its outer circumference directly opposite to the locking tabs, 10, on its inner vertical surface. The cap has an axially extending support, 8, that engages resilient sealing plug, 6, as by a snap ring, 40, shown in FIGS. 2 and 5. Further, the cap has a raised lip around its top surface, as shown in FIGS. 2 and 5. The lip serves as a guide for the insertion of a pressure sensitive label, used for recording the date of the specimen and the signatures of the donor and the collector. This label is of the type which cannot be removed without being at least partially destroyed.

Figure 8:
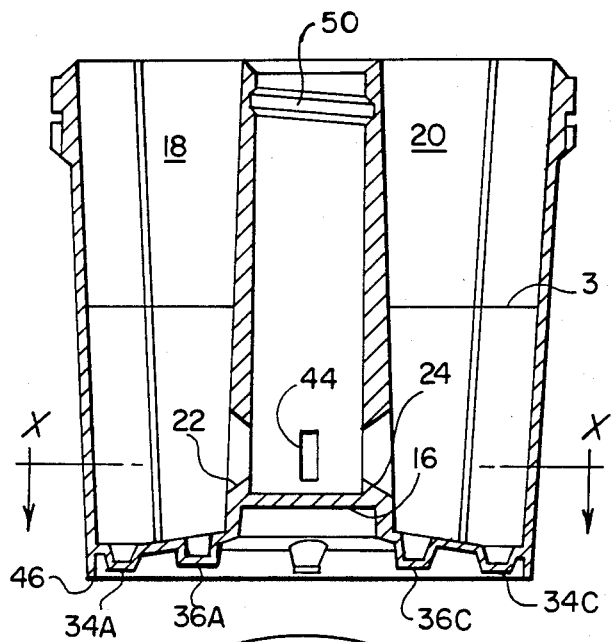
FIG. 8 is a side elevation view, in partial section, of the base cup shown in FIG. 3.

With reference to FIG. 8, urine poured axially into the container travels down the central receiving passageway, 30, out through four equal distribution ports (22, 24, 42, 44), and into each of four fluid receiving chambers (A, B, C, D). The ports are spaced above the transverse wall, 16, so that no more than 10 cc. of urine can enter one receiving chamber without an equalizing overflow distribution being effected into each of the other receiving chambers. In this manner, substantially equal volumes of urine flow at the same time into each chamber. Any off-axis urine collection can be redistributed by tilting the cup until the urine level is higher than the horizontal section line x—x, as shown in FIG. 8. An optional handle (not illustrated) can have a semi or full circular portion that will slip up from the bottom of the cup to engage around the outer circumference of the cup, for example, between the cup ratchet guides 26 and the section line x—x. In that fashion, remote placement of the cup open upper end can be facilitated, during the specimen collection task.

Figure 9:
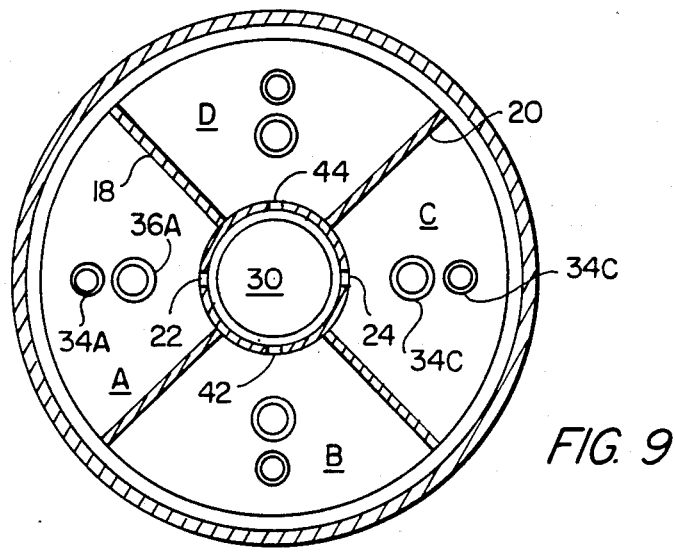
FIG. 9 is a top plan view, in partial section, taken along Line x—x, of the base cup shown in FIG. 8.
Figure 7:
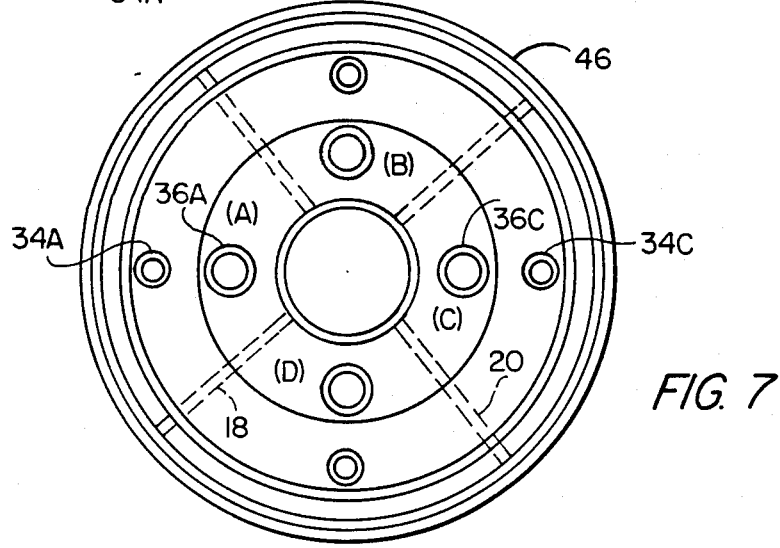
FIG. 7 is a bottom plan view of the base cup shown in FIG. 3.

As shown in FIGS. 7, 8, and 9, the compartments A, B, C, D, are separated by four vertically extending, substantially planar, partitions. For example, chambers A and D are separated by planar member, 18, while chambers C and D are separated by planar member, 20. The bottom surfaces of the set of drain nipples (34A, 34B, 34C, 34D) and the set of vent nipples (36A, 36B, 36C, 36D) are protected from damage by a downwardly extending rim, 46, as shown in FIG. 8. The resilient plug, 6, is configured to pass axially and downwardly into a substantially right circular cylinder central receiving passageway 30, and then become radially expanded upon a contact with the upper surface of transverse wall element, 16. The bottom surface of each equal distribution port (22, 24, 42, 44) is spaced slightly above that transverse wall, 16, in order to provide a seat for the distal end of the plug. A slight radial expansion occurs upon an axial compression of the sealing plug, 6, so as to create a slight bulging of rubber into each axially elongated, substantially rectangular equal distribution port (22, 24, 42, 44).

After collection of a urine specimen, the cap, 4, is placed over the base cup, 2, and turned clockwise approximately 1/16 of a turn, until the twist lock cap tabs (10) engage against the twist lock cup tabs, 12, as discussed hereinbefore. The opposed ramp surfaces, 13 and 17, act as the first engagement means to force the cap axially down, and squeeze the annular seal, 5, down against the upper edges of the cup, 4. The downward extensions, 15, prevent over-rotation, and will frangibly break off if an over-rotation is forced. The first engagement mode occurs simultaneously at all mating locking tabs (10, 12). Only a short rotation is needed to force the cap down, since each cap lock tab, 10, initially is located in a resting position on top of one of the circumferentially disposed cup ratchet guides, 26. As shown in FIG. 3, the vertical clearance space, 28, below the bottom edge of the extension, 15, is not sufficient to pass a cap locking tab, 10, past the point of total ramp surface engagement shown in FIG. 3.

A second engagement means is simultaneously supplied by engagement of a continous male thread member, 48, (or discrete extending bosses) into the female thread channel, 50, as shown occuring in FIG. 1. The cap, optionally, may simply have a snap-ring second engagement means that is initiated with the aid of a slight axial motion supplied by the first locking engagement means. FIG. 5 shows a slightly inclined thread element, 48, surrounding a medial portion of the resilient plug support, 8. FIG. 8 illustrates a central receiving passageway, 30, with a slightly inclined female thread element, 50. This second engagement means permits the central portion of the cap to assist in compressing the flat annular seal, 5, tightly against the top edges of the cup. If the cap, 4, is forcibly over-rotated upon the base cup, 2, there will be visible deformation of all the downward extending legs, 15, on all of the cap locking tabs, 12. A reverse rotation will be even more difficult, since the leading edges of each cup ratchet guide, 26, will abut the trailing edges of each cap locking tab, 10, after the cap is rotated to engage as shown in FIG. 3.

When an analytical test is to be performed on the specimen aliquot within chamber A, for example, the hollow-wall drain nipple, 3A, is cut off with a provided cutting blade, scissor, scalpel. The hollow-wall vent nipple, 36A, is cut off in like manner. Once the drain and vent nipples are cut off there is no way to reapply the deformed, cut-off portions. Therefore, a simple inspection reveals whether the specimen has been accessed after the initial sealing step.

While a preferred embodiment of the invention has been shown and described, the invention is to be defined by the scope of the appended claims:

We claim:

1. An improved urine specimen collection vessel comprising a substantially cylindrical base cup, a cap adapted to be superposed thereon, and a means to sealing engage and to lock the cap upon the base cup and resist subsequent removal of the cap from the base cup once sealingly engaged and locked, wherein the base cup further comprises a plurality of upwardly open chambers disposed circumferentially around a central receiving passageway having a tubular wall, a set of equal distribution ports within said tubular wall to communicate said central receiving passageway with each of said surrounding chambers, and means to permit access into a chamber through an exterior wall portion of the base cup, wherein further the means to sealingly engage and lock the cap comprises a first means to sealingly engage against an upper portion of said base cup and a second means to sealingly engage against said equal distribution ports, when the cap is locked upon the base cup.

2. A urine collection vessel according to claim 1, wherein the first sealing means further comprises an annular seal located at a lower surface of said cap, said equal distribution ports in said tubular wall are spaced above a transverse wall of said central receiving passageway that is spaced above a bottom surface of said base cup, and said central receiving passageway is substantially a right circular cylinder adapted to accept said second sealing means, and said second sealing means, further comprises a resilient sealing plug located at the distal end of an axial extension of said cap, wherein a position of first and second sealing engagement occurs when said cap is inserted onto said base cup and then axially displaced so as to simultaneously force said annular seal against upwardly open edges of said chambers while forcing said resilient plug against said transverse wall.

3. A urine specimen collection vessel according to claim 1, wherein the means to sealingly engage and to lock the cap upon the base cup further comprises a plurality of one-way rotation cap locking tabs and cup locking tabs as said first sealing means and said second sealing means further comprises a thread engagement between an axial extension of said cap, that is a support for a resilient sealing plug and an inner wall of said central receiving passageway, wherein said thread engagement is located between said first sealing means and said second sealing means, and said second sealing means further comprises said resilient sealing plug being mounted at the distal end of said support, and adapted to seal against said equal distribution ports.

4. A urine collection vessel according to claim 3, wherein the cap locking tabs and cup locking tabs have opposed ramp surfaces that engage upon a one-way rotation and vertical surfaces that resist a disengagement, wherein further a plurality of cup ratchet guides are spaced circumferentially around and below the cup locking tabs so as to initially guide said cap locking tabs into a locking engagement and thereafter abut said cap locking tabs and prevent a reverse rotation.

5. A urine collection vessel according to claim 1, wherein the means to permit access to each chamber comprises at least one hollow-wall nipple that is injection molded as part of a wall portion of the base cup that defines each chamber and extends outwardly therefrom.

6. A urine collection vessel according to claim 1, wherein four chambers of substantially equal volume are defined and separated from adjoining chambers by axially extending planar wall elements that extend radially between a central receiving passageway that is substantially a right circular cylinder and concentric with an outer wall of said base cup.

* * * * *